United States Patent
Detry et al.

(10) Patent No.: US 9,687,253 B2
(45) Date of Patent: Jun. 27, 2017

(54) BATTERY HOUSING FOR POWERED SURGICAL TOOL

(71) Applicant: Zimmer Surgical SA, Geneva (CH)

(72) Inventors: Marc Detry, Ayze (FR); Kévin Sornay, Saint Jorioz (FR)

(73) Assignee: Zimmer Surgical SA, Plan-les-Ouates (CH)

( * ) Notice: Subject to any disclaimer, the term of this patent is extended or adjusted under 35 U.S.C. 154(b) by 0 days.

(21) Appl. No.: 14/687,240

(22) Filed: Apr. 15, 2015

(65) Prior Publication Data

US 2015/0216538 A1 Aug. 6, 2015

Related U.S. Application Data

(63) Continuation of application No. 13/966,716, filed on Aug. 14, 2013, now Pat. No. 9,034,505, which is a continuation of application No. PCT/EP2011/070312, filed on Nov. 17, 2011.

(30) Foreign Application Priority Data

Feb. 15, 2011 (EP) .................................. 11154456

(51) Int. Cl.
*A61B 17/16* (2006.01)
*H01M 2/10* (2006.01)
*A61B 17/00* (2006.01)

(52) U.S. Cl.
CPC ....... *A61B 17/1628* (2013.01); *H01M 2/1022* (2013.01); *A61B 2017/00734* (2013.01); *H01M 2/10* (2013.01); *H01M 2220/30* (2013.01)

(58) Field of Classification Search
None
See application file for complete search history.

(56) References Cited

U.S. PATENT DOCUMENTS

| 9,034,505 B2 | 5/2015 | Detry et al. |
| 2003/0149424 A1* | 8/2003 | Barlev et al. ..................... 606/1 |
| 2013/0330589 A1* | 12/2013 | Detry ................. A61B 17/1628 429/100 |

FOREIGN PATENT DOCUMENTS

WO 2007090025 A1 8/2007

OTHER PUBLICATIONS

"U.S. Appl. No. 13/966,716, Notice of Allowance mailed Jan. 16, 2015", 13 pgs.

(Continued)

*Primary Examiner* — Patrick Ryan
*Assistant Examiner* — Carmen Lyles-Irving
(74) *Attorney, Agent, or Firm* — Schwegman Lundberg & Woessner, P.A.

(57) ABSTRACT

A battery housing for a driver of a powered surgical tool. The battery housing includes a casing with an opening for inserting at least one battery into the casing, a door for closing the opening when the door is in its closed position, and a driver interface for removably attaching the battery housing to a driver of a powered surgical tool. The door includes at least one part that is configured for being blocked by the driver when the door is moved out of its closed position and the battery housing is attached to the driver, such that the door cannot be opened when the battery housing is attached to the driver.

8 Claims, 3 Drawing Sheets

(56) References Cited

OTHER PUBLICATIONS

"Chinese Application Serial No. 201180066088.1, Response filed Sep. 7, 2015 to Office Action mailed Apr. 20, 2015", (W/ English Translation of Claims), 8 pgs.
"European Application Serial No. 11154456.5, Decision to Grant mailed Jun. 18, 2015", 2 pgs.
"European Application Serial No. 11154456.5, Intention to Grant mailed Jan. 28, 2015", 40 pgs.
"European Application Serial No. 11785400.0, Decision to Grant mailed Jun. 18, 2015", 2 pgs.
"European Application Serial No. 11785400.0, Intention to Grant mailed Jan. 28, 2015", 40 pgs.
"International Application Serial No. PCT/EP2011/070312, International Preliminary Report on Patentability mailed Feb. 12, 2013", 7 pgs.
"International Application Serial No. PCT/EP2011/070312, International Search Report mailed Mar. 5, 2012", 3 pgs.
"International Application Serial No. PCT/EP2011/070312, Written Opinion mailed Mar. 5, 2012", 4 pgs.

\* cited by examiner

BATTERY HOUSING FOR POWERED SURGICAL TOOL

CROSS-REFERENCE TO RELATED APPLICATIONS

This application is a continuation of U.S. patent application Ser. No. 13/966,716, now U.S. Pat. No. 9,034,505, filed Aug. 8, 2013, which is a continuation of PCT/EP2011/070312 filed on Nov. 17, 2011, which claims priority to EP11154456.5, filed on Feb. 15, 2011, the entire disclosures of which are incorporated herein by reference.

TECHNICAL FIELD

The present disclosure relates to a battery housing for powered surgical tools. The present disclosure relates in particular to a detachable battery housing containing one or more batteries for powering the motor of a powered surgical tool's driver.

BACKGROUND

Powered surgical tools, for example powered surgical saws and/or drills, are powered tools that surgeons employ for performing certain surgical procedures that include cutting and/or drilling bones and/or other tissues. A powered surgical tool typically comprises a handpiece, or driver, in which is housed a motor, for example an electrically or pneumatically driven motor. The motor is attached, for example through a drive shaft, to a head of the driver, which is adapted to removably receive a surgical tool, for example a saw blade or a drill bit. Depending on the configuration of the driver and/or the nature of the attached tool, the actuation of the motor causes an oscillating or rotating movement of the head and thus of the tool.

Powered surgical tools, in particular those with an electrically driven motor, usually comprise one or more batteries providing the electrical power necessary for driving the motor. The batteries are often contained in a housing having an opening for allowing the insertion and removal of the batteries therein, and for example a door for closing, preferably hermetically closing, the opening. The battery housing is often removably attached to the driver.

An advantage of removable batteries, is that they can be easily taken out of the powered tool, for example before sterilization. Indeed, while sterilization of the powered surgical tool is required for the patients' safety, electrical batteries often suffer from the related heat and humidity conditions that can lead to a significant loss of power. After and/or before an operation, the batteries are thus preferably taken out of the battery housing, which is then sterilized, for example in an autoclave, while the batteries are cleaned and disinfected. The batteries are then inserted again in to the sterilized battery housing and the housing is closed, thus forming a battery pack which is sterile on its outside despite containing non sterile battery or batteries.

Furthermore, the battery housing being for example removably attached to the driver of the powered tool, the battery pack can easily be replaced, if necessary, during an operation and inside an operation room, because no access to the unsterile batteries is necessary. If for any reasons the batteries need replacement, the battery housing can be detached from the driver and replaced by a fresh and sterile battery pack, without contamination risk for the patient. No battery housing thus needs to be opened for replacing batteries.

However, since the batteries inside the battery housing are not sterile, a contamination risk still exists if for example the battery housing inadvertently opens or remains open in the operation room, in particular if it opens or remained partly opened while the tool to which it is attached is being used.

There is thus a need for a battery housing and a corresponding powered surgical tool that can avoid any risk of contamination by preventing in particular the battery housing from being opened while the powered tool is being used.

SUMMARY

It is thus an object of the present disclosure to provide a safe battery housing for powered surgical tools.

It is in particular an aim of the present disclosure to provide a battery housing or container that cannot be opened while the powered surgical tool is being used or ready for use.

It is another aim of the present disclosure to provide a battery housing or container that cannot remain partly opened while the powered surgical tool is being used or ready for use.

These objects and other advantages are achieved by a battery housing, by a battery housing and driver assembly and by a powered surgical tool comprising the features of the corresponding independent claims.

These objects are furthermore achieved by a battery housing for a driver of a powered surgical tool, the battery housing comprising a casing with an opening for inserting at least one battery into the casing, a door for closing the opening when the door is in its closed position and a driver interface for removably attaching the battery housing to a driver of a powered surgical tool, wherein the door comprises at least one part that is configured for being blocked by the driver when the door is moved out of its closed position and the battery housing is attached to the driver, such that the door cannot be opened when the battery housing is attached to the driver.

These objects are also achieved in particular by a battery housing and driver assembly, comprising such a battery housing and a driver for a powered surgical tool, wherein the at least one part of the door is blocked by the driver when the door is in its closed position and when the battery housing is attached to the driver.

These objects are also achieved in particular by a powered surgical tool comprising such a battery housing and driver assembly and a surgical tool configured for attachment to the driver.

Accordingly, the door of the battery housing comprising one or more elements that are configured for being blocked by the driver upon an attempt to move the door out of its closed position while the battery housing is attached to a driver. The door is maintained closed as long as the driver is attached to the battery housing, thereby avoiding the inadvertent opening of the door while the powered surgical tool is in use, even if the door is not locked by a specific locking mechanism, e.g. the door's locking mechanism is opened or the door is lacking such a specific mechanism.

Furthermore, according to variant embodiments, the driver interface is configured such that the driver must be sled onto the battery housing and pushes the door in its closed position while being attached on to the battery housing. Accordingly, if the door is not completely closed before attaching the driver, it will be closed by the operation of attaching the driver to the battery housing.

In still variant embodiments, the door comprises a self-locking mechanism, thereby facilitating its locking, in particular when it is pushed in its closed position while the driver is being attached onto the battery housing.

BRIEF DESCRIPTION OF THE DRAWINGS

The above and further advantages of the disclosure will be better understood by reference to the following description illustrated by the figures, where.

DETAILED DESCRIPTION

Figure 1:
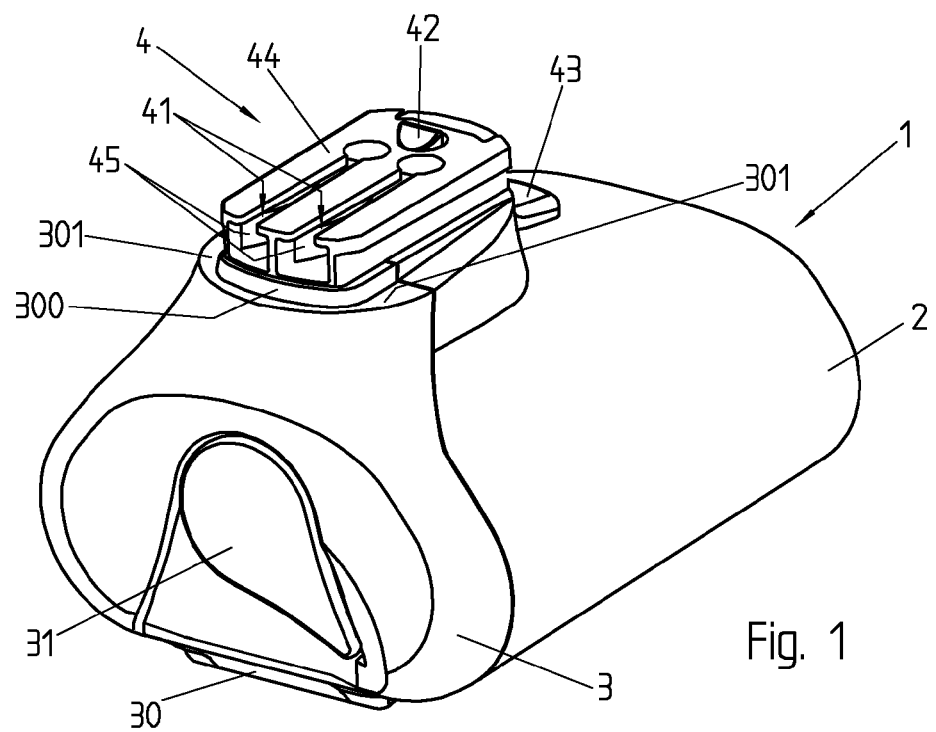
FIG. 1 is a perspective view of an illustrative but not limiting example of a battery housing according to an exemplary embodiment.

With reference to FIG. 1, the battery housing 1 is a closed container with a casing 2 having an opening, and a door 3 which is adapted and configured to close the opening. The battery housing 1 further comprises a driver interface 4 for removably attaching it to a driver of a powered surgical tool, not represented in FIG. 1, which comprise a correspondingly configured interface.

The driver interface 4 comprises attachment means for mechanically coupling the battery housing 1 to the driver. The attachment means for example comprises grooves 41 in which corresponding ridges of the driver's battery housing interface can slide when the battery housing 1 is being attached to the driver. In an embodiment, the attachment means further comprises a self-locking pin 42 that latches into a corresponding opening of the driver's battery housing interface when the battery housing 1 is correctly attached to the driver, thereby locking the battery housing 1 onto the driver for avoiding any undesired detachment of the battery housing 1. The self-locking pin 42 is actuated by a lever 43 that allows retracting it before detaching the battery housing 1 from the driver. The lever 43 for example act against the elastic force of one or more springs, not visible in FIG. 1, that maintain the self-locking pin 42 in its locked, or extended, position. In a variant embodiment, the self-locking pin and the lever for actuating it is comprised in the battery interface of the driver, while the driver interface of the battery housing comprises a corresponding opening in which the self-locking pin latches when the battery housing is correctly attached to the driver.

The driver interface 4 further comprises electrical contacts 45 for electrically coupling the battery housing 1 to the driver, in particular for establishing an electrical contact between the poles of the one or more batteries contained in the battery housing and the driver's electrical motor for powering said motor. The electrical contacts 45 are for example located in the grooves 41 where they are in contact with corresponding electrical contacts located around the ridges of the driver's battery housing interface, when the battery housing 1 is attached to the driver. Other configurations and/or position of the electrical contacts are however possible within the frame of the present invention.

The casing 2 comprises an opening, for example on a front side of the casing 2, for inserting one or more batteries therein. The opening can be closed, for example hermetically closed, by a door 3. The door 3 is for example pivotably attached on one side to the casing 2 through a hinge 30. In embodiments, when closed the door 3 is locked and can be unlocked for example by actuating, e.g. rotating, a handle 31 located on the external side of the door 3. The handle 31 actuates a locking mechanism located for example on the inner side of and/or inside the door 3.

According to the invention, the door 3 is configured such that it cannot be opened when the battery housing 1 is attached to a driver, even if the locking mechanism is unlocked.

In embodiments, the door 3 is pivotably attached to the casing 2 with its hinge side located opposite to the driver interface 4 such that its swing side is close to or adjacent the driver interface 4 when the door 3 is in its closed position. The door 3 is configured such that, when the door 3 is in its closed position and the battery housing 1 is attached to a driver, at least a part of the door's swing side is blocked against any opening movement by the driver, thereby preventing the door 3 from opening. The swing side of the door 3 is thus maintained close to the driver interface 4 by the driver when the battery housing 1 is attached to a driver.

In the illustrated embodiment, a lip 300 formed on at least part of the edge of the swing side of the door 3 is part of the driver interface 4 when the door 3 is closed, such that its movements are strictly limited or at all prevented by the battery interface of a driver that would be attached to the battery housing 1.

In embodiments, the door 3 comprises wings or projections 301 on its swing side, which extend beyond the rotation axis of the hinge 30 towards a back or body side of the casing 2 when the door is in its closed position. The projections 301 thus extend from the swing side of the door 3 in a direction essentially perpendicular to the principal plane of the door 3, i.e. essentially radial relative to the axis of the hinge 30, such that when the door 3 is rotated around the hinge 30 the top of the projections 301 being further away from the rotation axis than the rest of the swing side of the door 3, they move along an arch having a larger radius than the radius along which the rest of the swing side moves. As a result, when the door 3 is opened, at least part of the projections 301, in particular their tip, first moves, in its circular movement, towards a surface 44 of the driver interface before moving away from it and freeing the opening in the front side of the casing 2. Accordingly, if a driver is attached to the driver interface 4, the projections 301, and in particular their tip, would come into contact with the attached driver, thereby preventing the door 3 from being opened.

Other configurations, in particular other shapes of the door 3, are possible in order to prevent the door 3 from being opened when a driver is attached to the driver interface 4.

Figure 2:
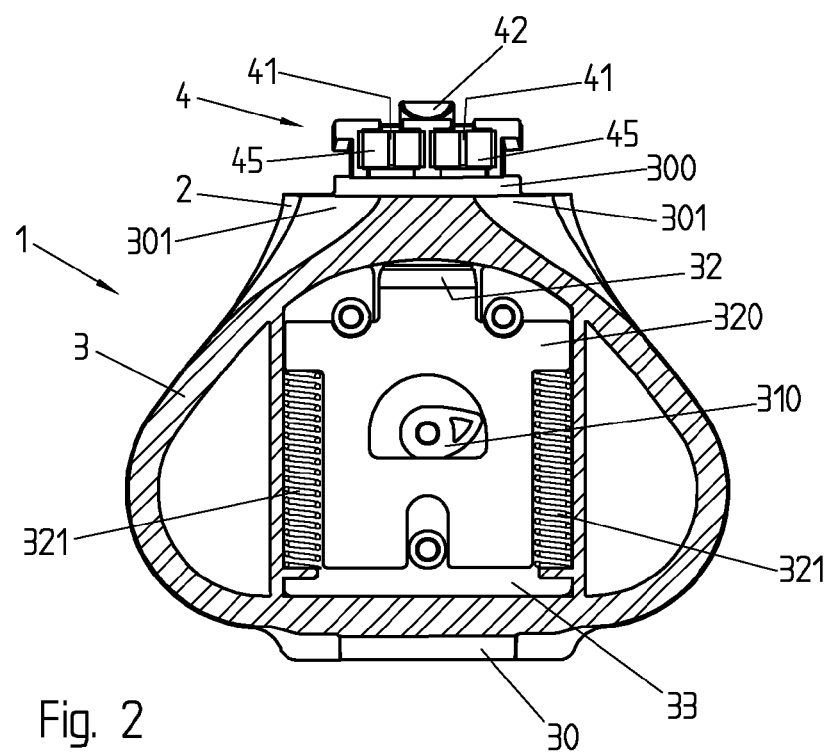
FIG. 2 is a transversal cut view of the battery housing of FIG. 1 showing the door locking mechanism in it locked position.
Figure 3:
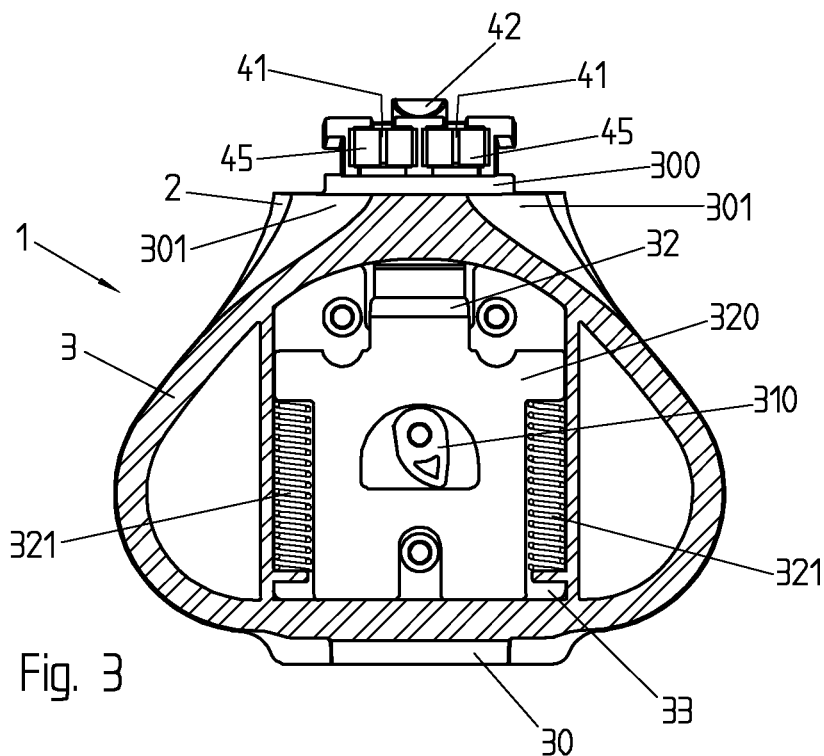
FIG. 3 is a transversal cut view of the battery housing of FIG. 1 showing the door locking mechanism in its unlocked position.

In embodiments, the door 3 comprises a self-locking mechanism, which is illustrated by way of an exemplary embodiment in FIG. 2 and FIG. 3, such that the door 3 is automatically locked when it is pushed in its closed position against the casing 2.

Figure 4:
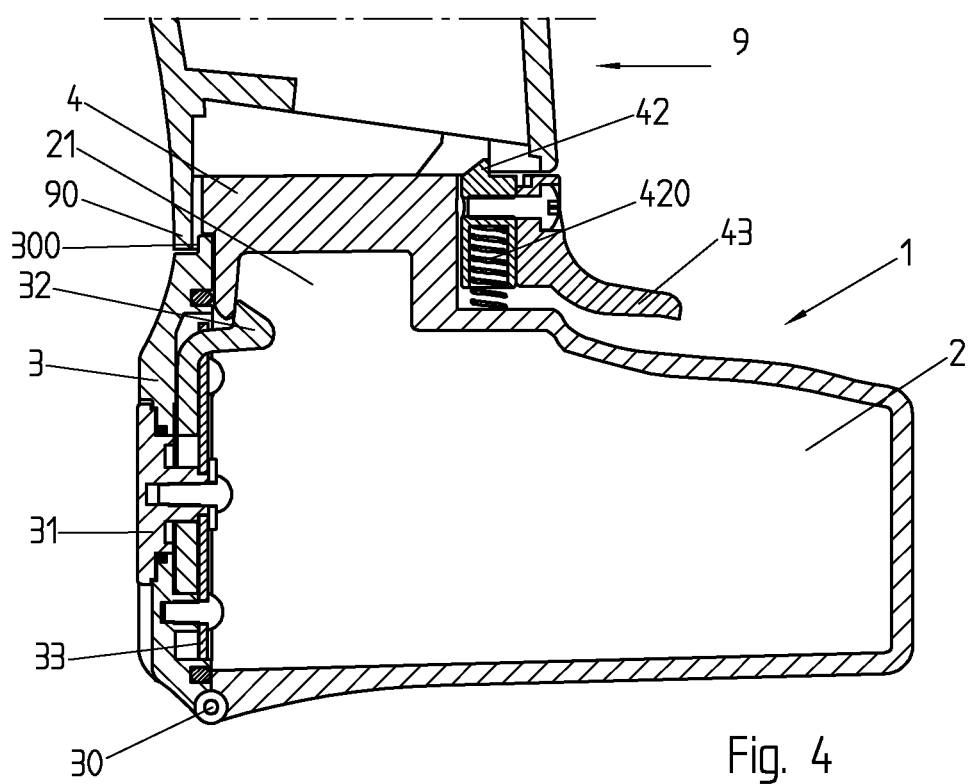
FIG. 4 is a lateral cut view of the battery housing of FIG. 1 and of a part of an exemplary adapted driver.

In the illustrated exemplary embodiment, the self-locking mechanism comprises a latch 32 that cooperates with a notch 21 of the casing 2, visible in FIG. 4, for maintaining the door 3 in its closed position when the self-locking mechanism is in its locked position. The latch 32 is for example pushed into its locked position by the force of one or more spring elements, for example by two springs 321 that push on a base plate 320 to which the latch 32 is attached in a fixed relationship. The latch 32 is for example integral to the base plate 320. The latch 32 is for example profiled such that when the door 3 is being pushed into its closed position, the latch 32 comes in contact with the notch 21 and is pushed towards it unlocked position against the force of the springs 321. Once the door 3 is closed, the latch 32 is returned by the force of the springs 321 into its locked position behind the notch 21, thereby maintaining the door 3 in its closed position.

The self-locking mechanism is for example actuated, in particular pushed in its unlocked position, by a cam 310 that can act on the base plate 320 for displacing it. The cam 310 is for example located in an aperture of the base plate 320, whereas the cam 310 and the aperture in the base plate 320 are configured such that when the cam 310 is rotated, it pushes on the base plate 320 in a direction opposed to the direction of the force exerted by the springs 321, thus pushing the latch 32 in its unlocked position. The cam 310 is connected to the handle 31 located for example on the external side of the door 3, and is rotated by the rotation of the handle 31. In an embodiment, the cam 310 is for example integral with the handle 31. FIG. 3 illustrates an exemplary embodiment of the door's self-locking mechanism in its unlocked position.

The self-locking mechanism is for example attached to the inner side of the door 3 and covered in an embodiment by a cover plate 33 that protects the self-locking mechanism against external elements. The cover plate 33 is for example riveted or screwed onto the inner side of the door 3.

FIG. 4 illustrates the exemplary battery housing 1 removably attached to a corresponding driver 9.

In embodiments, the driver interface 4 comprises parts of both the casing 2 and of the door 3. In the illustrated embodiment, the driver interface 4 is for the most part integral with the casing 2 and comprises a part of the door 3, for example a lip 300 on the edge of the swing side of the door 3. When the driver 9 is attached and locked onto the battery housing 1 and the door 3 is closed, the lip 300 is thus maintained together with the other elements of the driver interface 4 by the driver 9, thereby preventing the door 3 from being opened even if the door's self-locking mechanism is inadvertently unlocked. In the illustrated embodiment, a flange 90 of the battery interface of the driver for example blocks the part 300 of the door 3 when the driver 9 is attached to the battery housing 1.

Figure 5:
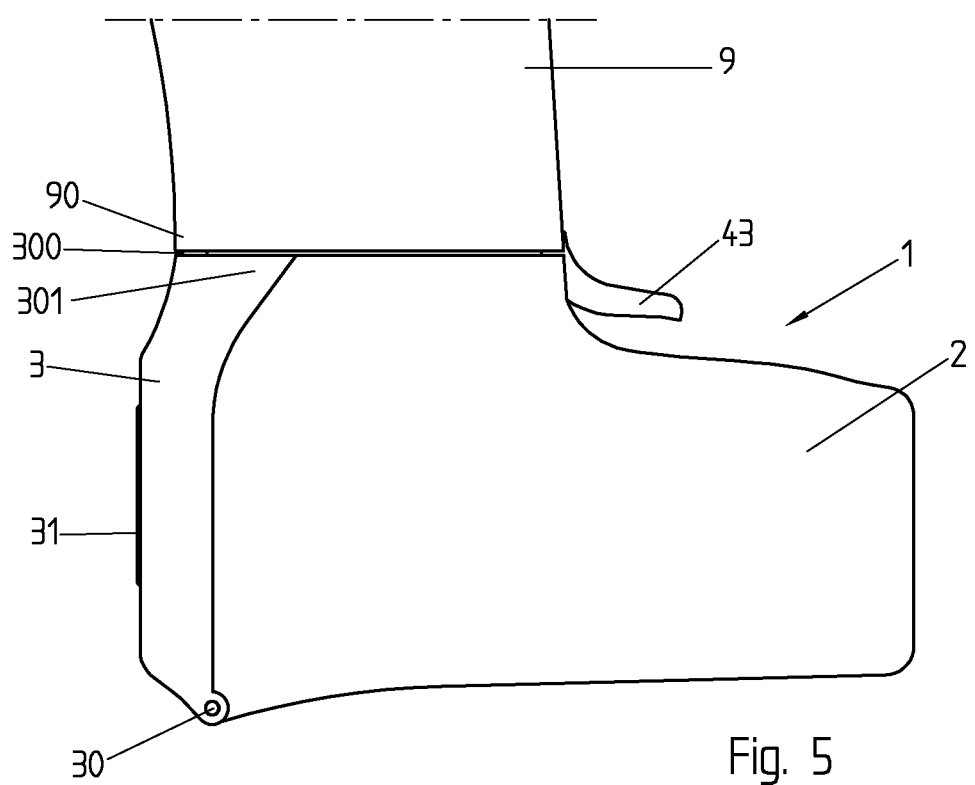
FIG. 5 is a lateral view of the battery housing of FIG. 1 and of a part of an exemplary adapted driver.

In embodiments, as illustrated in FIG. 5, the projections 310 extending in a direction essentially perpendicular to the plane of the door 3 and beyond the rotation axis of hinge 30 towards the body side of the battery housing 2 when the door 3 is closed, prevent the door 3 from being opened when the battery housing 1 is attached to a driver 9. Indeed, if the door 3 was to be rotated out of its closed position around the hinge 30, the projections 310 would start moving towards the driver 9 and rapidly abut against it, thereby preventing the door 3 from moving any further. Accordingly, the door 3 of the battery housing 1 cannot be opened while the driver 9 is correctly attached to the battery housing 1, thereby preventing it in particular from being opened while the corresponding powered surgical tool is in use.

In the illustrated exemplary but in no way limiting embodiment, when a driver is attached to the battery housing 1, the door 3 is maintained in its closed position by both the lip 300 and the projections 301 that are configured to rapidly abut against the driver 9, for example against its lower flange 90, when the door 3 is rotated out of its closed position. The one skilled in the art will however understand that the opening of the door when a driver is attached to the battery housing 1 can be prevented by only one of these elements, or even by only one projection, configured to be blocked by the driver when the door is rotated out of its closed position. In addition to or in replacement of the illustrated lip and projections, the door can comprise other elements having for example other shapes and/or position on the door, that are blocked by the driver for preventing the door from being opened when a driver is attached to the battery housing.

In embodiments, the driver 9 is attached to the battery housing 1 by being sled onto the battery housing 1, in particular onto the driver interface 4, from the front side of the battery housing 1 where the door 3 is located towards the back side, or body side, of the battery housing 1, such that if the door 3 is only partly closed, the interface flange 90 of the driver 9 holds onto the lip 300 and/or on the projections 310 and pushes them against the other elements of the driver interface 4 until the driver 9 is locked onto the battery housing 1, for example by the self-locking pin 42, thereby pushing the door 3 in its closed position until it is locked by its self-locking mechanism. Accordingly, if the door 3 is only partly closed and thus unlocked, it will be correctly closed and locked when the driver 9 will be attached to the battery housing 1, thereby preventing the use of the corresponding powered surgical tool with the door 3 partly opened.

In variant embodiments, the door further comprises electrical contacts that are in contact with corresponding electrical contacts of the casing when the door is closed and locked. When the door is open or partly opened, the electrical contacts of the door are taken away from the electrical contacts of the casing thereby opening the thus formed electrical switches and interrupting for example the electrical power supply to the driver, such that the driver's motor can not be powered by the battery or batteries when the door of the battery housing is opened and/or unlocked.

The casing 2 and the door 3 are for example made of rigid plastic material that is compatible with medical applications and can thus be sterilized in autoclaves. Some elements like the self-locking pin 42 and/or parts of the door's self-locking mechanism can be made of one or more medically compatible metals or alloys. The springs 321 of the self-locking mechanism, the spring 420 of the self-locking pin 42 and the electrical contacts 45 are advantageously made of metal.

The illustrated embodiment described herein is given as illustrating but in no way limiting example. Other configurations of the door's self-locking mechanism and/or of the driver interface's attachment means, in particular, are possible within the frame of the invention.

The invention claimed is:

1. A powered surgical tool, comprising:
   a driver; and
   a battery housing detachably coupleable to the driver, the battery housing including:
   a casing with an opening for inserting at least one battery into the casing;
   a door for closing the opening when the door is in a closed position, the door extending from a hinge side to an opposing swing side, the door being pivotally attached to the casing on the hinge side with a hinge;
   a driver interface for removably attaching the battery housing to the driver of the powered surgical tool;
   an internal locking structure for locking the door in the closed position; and
   an external locking structure for locking the door in the closed position when the battery housing is attached to the driver, wherein the external locking structure only retains the door in a closed position when the battery housing is attached to the driver and the external locking structure engages an interface flange of the driver with the door in a partly closed position to transition the door to a fully closed position as the driver is locked into the driver interface.

2. The battery housing of claim 1, wherein when the door is in the closed position and the battery housing is attached to the driver, the external locking structure prevents the door from opening even if the internal locking structure is unlocked.

3. The battery housing of claim 1, wherein the external locking structure includes a mechanical engagement between the driver and the battery housing.

4. The battery housing of claim 1, wherein a portion of the swing side of the door forms at least a portion of the external locking structure.

5. The battery housing of claim 1, wherein a portion of the driver forms at least a portion of the external locking structure.

6. The battery housing of claim 1, wherein the swing side of the door is adjacent the driver interface when the door is in the closed position.

7. The battery housing of claim 1, wherein a portion of the swing side of the door forms a portion of the driver interface when the door is in the closed position.

8. The battery housing of claim 7, wherein the portion of the driver interface formed by the swing side of the door forms at least a portion of the external locking structure.

\* \* \* \* \*

UNITED STATES PATENT AND TRADEMARK OFFICE
CERTIFICATE OF CORRECTION

PATENT NO. : 9,687,253 B2  
APPLICATION NO. : 14/687240  
DATED : June 27, 2017  
INVENTOR(S) : Detry et al.

Page 1 of 1

It is certified that error appears in the above-identified patent and that said Letters Patent is hereby corrected as shown below:

On the Title Page

In item (73), in "Assignee", in Column 1, Line 1, delete "Plan-les-Ouates" and insert --Geneva-- therefor In item (30), in "Foreign Application Priority Data", in Column 1, Line 1, delete "11154456" and insert --11154456.5-- therefor Signed and Sealed this
Twelfth Day of June, 2018

Andrei Iancu
*Director of the United States Patent and Trademark Office*